US00RE35804E

United States Patent [19]

Stewart

[11] E Patent Number: Re. 35,804

[45] Reissued Date of Patent: May 26, 1998

[54] SYSTEMS AND METHODS FOR REMOVING UNDESIRED MATTER FROM BLOOD CELLS

[75] Inventor: Mary A. Stewart, Mundelein, Ill.

[73] Assignee: Baxter International Inc., Deerfield, Ill.

[21] Appl. No.: 26,516

[22] Filed: Mar. 4, 1993

Related U.S. Patent Documents

Reissue of:

[64] Patent No.: 4,997,577
Issued: Mar. 5, 1991
Appl. No.: 453,952
Filed: Dec. 20, 1989

[51] Int. Cl.[6] ..... B01D 37/00; B01D 24/02; B01D 35/01; A61B 19/00

[52] U.S. Cl. ..... 210/767; 210/233; 210/257.1; 210/420; 210/436; 210/472; 422/41; 422/44; 604/406; 604/410

[58] Field of Search ..... 210/767, 787, 210/805, 196, 233, 257.1, 420, 436, 472; 422/41, 44; 604/29, 406, 408, 410

[56] References Cited

U.S. PATENT DOCUMENTS

| | | | |
|---|---|---|---|
| 4,157,723 | 6/1979 | Granzow et al. | 141/1 |
| 4,265,280 | 5/1981 | Ammann et al. | 141/98 |
| 4,396,382 | 8/1983 | Goldhaber | 604/28 |
| 4,412,835 | 11/1983 | Spencer | 604/29 |
| 4,439,179 | 3/1984 | Lueders et al. | 604/29 |
| 4,596,657 | 6/1986 | Wisdom | 210/257.1 |
| 4,767,541 | 8/1988 | Wisdom | 210/787 |
| 4,810,378 | 3/1989 | Carmen et al. | 210/257.1 |
| 4,855,063 | 8/1989 | Carmen et al. | 210/787 |
| 4,915,847 | 4/1990 | Dillon et al. | 604/410 |
| 4,915,848 | 4/1990 | Carmen et al. | 422/41 |
| 4,917,804 | 4/1990 | Franks et al. | 604/410 |
| 4,919,823 | 4/1990 | Wisdom | 210/787 |

*Primary Examiner*—John Kim
*Attorney, Agent, or Firm*—Daniel D. Ryan; Denise M. Serewicz; Bradford R. L. Price

[57] ABSTRACT

Systems and methods of collecting blood cells, substantially free of undesired matter, use a first container, that forms a part of a blood collection system, to initially collect a quantity of blood cells. A filtration system is then attached to the first container. The filtration system includes a second container, a first fluid path that leads to the second container through a filtration device, and a second fluid path that leads to the second container bypassing the filtration device. The blood cells are conveyed from the first container through the first fluid path and filtration device and into the second container to separate the undesired matter from the blood cells. The blood cells, now substantially free of the undesired matter, are then conveyed from the second container through the second fluid path, bypassing the filtration device, and back into the first container. The filtration system is then detached from the blood collection system.

24 Claims, 3 Drawing Sheets

SYSTEMS AND METHODS FOR REMOVING UNDESIRED MATTER FROM BLOOD CELLS

Matter enclosed in heavy brackets [ ] appears in the original patent but forms no part of this reissue specification; matter printed in italics indicates the additions made by reissue.

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Most of the whole blood collected from volunteer donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding: and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere) the red blood cells can be stored upwards to forty-two days (depending upon the type of anticoagulant and storage medium used); the platelet concentrate can be stored upwards to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cell substantially free of the white blood cell components, particularly for recipients who undergo frequent transfusions.

One way to remove white blood cells is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cells is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline white blood cell filtration device is used. The filtration can thereby be accomplished in a closed system. However, in these arrangements, the filtration process ultimately results in transferring the red blood cells out of the primary blood collection bag and into another bag for storage. Therefore, the filtration process requires both a primary blood collection bag and a second blood storage bag, both of which are subject to relatively stringent governmental regulations relating to blood containers.

Therefore, a need still exists for systems and methods for removing undesired matter from blood components prior to transfusion or storage in a way that lends itself to use in closed system environments, but which do not necessarily require the use of additional blood storage containers that are subject to stringent governmental regulations.

SUMMARY OF THE INVENTION

One aspect of the invention provides a blood collection system that comprises an assembly for collecting blood cells and an assembly for separating undesired matter from blood cells prior to storage or transfusion. The blood cells are initially collected and processed in the blood collection assembly. The separation assembly is then temporarily attached to the blood collection assembly. The blood cells are transferred into the attached separation assembly to remove undesired matter. The blood cells are then immediately returned to the blood collection assembly for storage and transfusion, and the separation assembly is detached.

In accordance with this aspect of the invention, the blood collection assembly includes a primary container that serves both as the container in which the blood cells are collected during processing and the container in which the blood cells are ultimately returned for storage after undesired matter is removed. The separation assembly includes a transfer container that comes into contact with the blood for only a short period of time during the separation process. This is because the blood separation assembly is only temporarily attached to the collection assembly during the separation process, and is then detached.

Another aspect of the invention provides a blood separation assembly having a temporary transfer container that is connected to two distinct fluid paths. The first fluid path has an inline separation device for separating the undesired matter from the blood cells. The second fluid path, however, bypasses the separation device. A flow control mechanism is associated with the first and second flow paths and is operable in two modes: one in which blood is conveyed through the first path, and another in which blood is conveyed through the second path.

When the separation assembly is attached to a blood collection container, and the flow control mechanism is placed in its first mode, blood cells can be conveyed from the collection container through the first flow path, and thereby through separation device, into the transfer container. In the process, the undesired matter is removed from the blood cells. Then, when the flow control means is placed in its second mode, the blood cells, now substantially free of the undesired matter, can be returned from the transfer container through the second flow path directly back to the collection container for storage or transfusion, altogether bypassing the separation device.

Since blood cells occupy the separation assembly for only a short period of time, the transfer container, as well as the entire separation assembly itself, need not be subject to the stringent governmental regulations pertaining to long term blood storage containers. Preferably, the separation assembly comprises a separate assembly that is temporarily joined to the blood collection container only during the separation process.

In a preferred embodiment of this aspect of the invention, the blood collection assembly and the separation assembly each comprises a sterile, closed system. In this arrangement, a sterile connection assembly attaches and detaches the collection and separation assemblies to preserve the sterile, closed integrity of both systems. Unwanted matter can thereby be removed from blood cells and the blood cells returned to their storage container without involving a single "non-sterile" entry into the system, and thereby without adversely effecting the quality of the blood products or the length of their storage periods.

Another aspect of the invention provides a method of collecting blood cells for storage substantially free of undesired matter. The method comprises the steps of collecting a quantity of blood cells in a first container that forms a part of a blood collection system. The blood is then conveyed into a separation system that includes a second container to which first and second fluid paths are attached. The first path includes a separation device for separating the undesired matter from the blood cells. The second path bypasses the separation device.

In accordance with this aspect of the invention, the blood cells are conveyed from the first container through the first fluid path and separation device and thence into the second container, thereby separating the undesired matter from the blood cells. The blood cells, now substantially free of the undesired matter, are then returned from the second container through the second fluid path, bypassing the separation device, and back into the first container for storage or transfusion. The separation system can then be removed from the blood collection system.

The invention provides blood processing systems and methods in which separation is accomplished using a temporary transfer bag assembly that need not be subject to stringent governmental regulations, and in which the bag that serves as the blood collection container prior to separation also serves as the blood storage container after separation.

The systems and methods that embody the features of the invention are particularly well suited for use in association with closed blood collection systems and conventional sterile connection techniques, thereby permitting separation to occur in a sterile, closed environment.

*Another aspect of the invention provides an assembly for removing undesired matter from blood cells comprising a filter body having an inlet and an outlet, and filtration medium in the filter body for removing undesired matter from blood cells. The assembly further comprises an inlet fluid path communicating with the inlet of the filter body and including means for attaching a first container holding a quantity of blood cells for conveying blood cells from the first container to the filtration medium for the removal of undesired matter. The assembly further comprises an outlet fluid path communicating with the outlet of the filter body for conveying blood cells from the filtration medium substantially free of undesired matter. The outlet fluid path includes a second container for receiving blood cells substantially free of undesired matter. The assembly further comprises a bypass path having opposite ends, one end being attached to the inlet fluid path between the first container and the inlet of the filter body and the opposite end being attached to the outlet fluid path between the second container and the outlet of the filter body for venting air without transferring liquid between the inlet fluid path and the outlet fluid path, bypassing the filtration medium in the filter body.*

While the systems and methods that embody the features of the invention can be used to process all types of blood components, they are well suited for the removal of white blood cells from red blood cells by filtration prior to transfusion or long term storage.

Other features and advantages of the invention will become apparent upon review of the following description, drawings, and appended claims.

DESCRIPTION OF THE PREFERRED EMBODIMENTS

Figure 1:
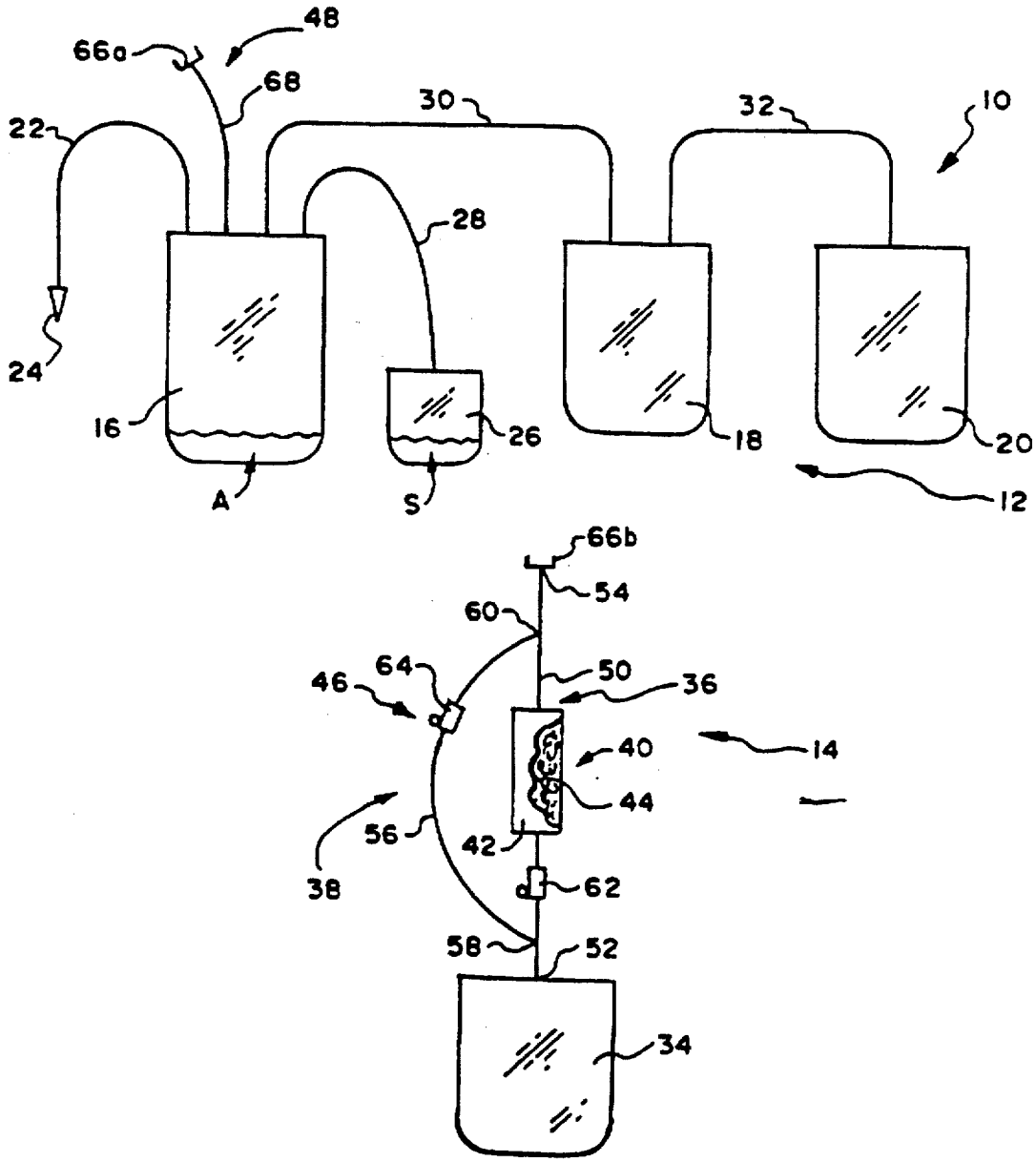
FIG. 1 is a schematic view of a blood collection system that includes a blood processing assembly and a blood filtration assembly that embody the features of the invention.

A blood collection system 10 is shown in FIG. 1. The system 10 comprises a blood collection, processing and storage assembly 12 and a separation assembly 14.

In the illustrated embodiment, the separation assembly 14 serves to remove undesired matter from blood cells by filtration. For this reason, it will be referred to as a "filtration" assembly. It should be appreciated, however, that separation can occur by various centrifugal and noncentrifugal techniques, and not merely "filtration" in the technical sense. Separation can occur by absorption, columns, chemical, electrical, and electromagnetic means. The term "filtration assembly" is broadly used in this specification encompass all of these separation techniques as well.

In the illustrated and preferred embodiment shown in FIG. 1, the filtration assembly 14 comprises an initially separate subassembly not joined to the blood processing assembly 12. This arrangement serves to reduce the regulatory requirements for the filtration assembly 14. It should be appreciated, however, that the filtration assembly 14 can be made as an integral part of the processing assembly 12.

The blood collection and storage assembly 12 comprises a multiple blood bag system having a primary bag or container 16 and one or more integrally attached transfer bags or containers 18 and 20. In use, the primary bag 16 (which is typically also called a donor bag) receives whole blood from a donor through integrally attached donor tubing 22 that carries an phlebotomy needle 24. A suitable anticoagulant A is contained in the primary bag 16.

In use, the primary bag 16 also serves as the storage container for the red blood cells processed in the assembly 12. A satellite bag 26 is attached to the primary bag 16 by integrally attached tubing 28. The satellite bag 26 contains a suitable storage solution S for the red blood cells. One such solution is disclosed in Grode et al U.S. Pat. No. 4,267,269.

The transfer bags 18 and 20 are attached to the primary bag 16 by integrally attached transfer tubing 30 and 32. The transfer bags 18 and 20 are intended to receive the platelet and plasma blood components for processing. The first transfer bag 18 ultimately serves as the storage container for the platelet concentrate, and the second transfer bag 20 ultimately serves as the storage container for the platelet-poor plasma.

All of the bags and tubing associated with the processing assembly 12 can be made from conventional approved medical grade plastic materials, such as polyvinyl chloride plasticized with di-2-ethylhexylphthalate (DEHP). Alternatively, the first transfer container 18, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTM). These materials, when compared to DEHP-plasticized polyvinyl chloride materials, have greater gas permeability that is beneficial for platelet storage.

The blood collection and storage assembly 12, once sterilized, constitutes a sterile, "closed" system, as judged by the applicable standards in the United States.

Figure 2:
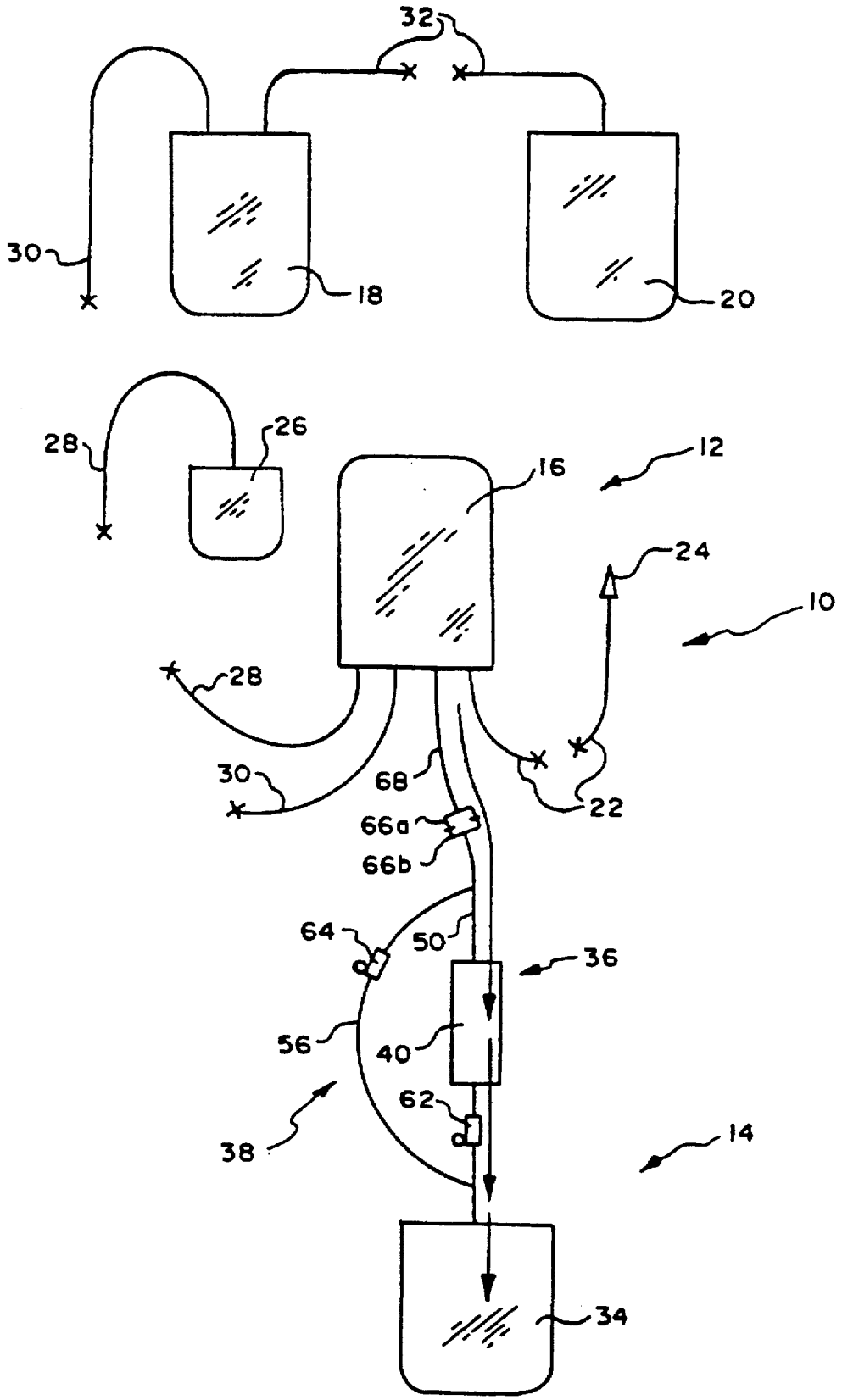
FIG. 2 is a schematic view of the system shown in FIG. 1, with the blood filtration assembly attached to the blood processing assembly for the purpose of removing undesired matter from the blood cells.

Whole blood is collected and then separated into its various therapeutic components within the assembly 12. These therapeutic components are typically red blood cells, plasma, and platelets. In use, the collected whole blood is centrifugally separated within the primary bag 16 into red blood cells and platelet-rich plasma. The platelet-rich plasma is transferred by conventional techniques into the first transfer bag 30, leaving the red blood cells in the primary bag. The transfer bags 18 and 20 are detached in a sterile fashion using a conventional heat sealing device (for example, the Hematron® dielectric sealer sold by Baxter Healthcare Corporation), which forms a hermetic, snap-apart seal in the tubing 30 (this seal is schematically shown by an "x" in FIGS. 2 to 4). The red blood cell storage solution S is transferred into the primary container 16, and the satellite bag 26 is also disconnected using the snap-apart seal "x" (as shown in FIG. 2). The donor tubing 22 is sealed and disconnected in the same fashion (as also shown in FIG. 2).

The platelet-rich plasma undergoes subsequent centrifugal separation within the first transfer bag 18 into platelet concentrate and platelet-poor plasma. The platelet-poor plasma is transferred into the second transfer bag 20, leaving the platelet concentrate in the first transfer bag 18. The transfer bags 18 and 20 are then separated by the snap-apart seals "x" in the tubing 32 (as shown in FIG. 2) for subsequent storage of the collected components.

The filtration assembly 14 includes a temporary transfer container 34 and two associated fluid flow paths 36 and 38. The temporary transfer container 34, as well as the entire filtration assembly 14 itself, are preferably provided in a "dry" condition, free of any fluids, storage mediums, and the like (except for any entrapped air), thereby avoiding regulatory requirements governing fluid-containing systems.

The first fluid path 36 includes an inline filtration device 40 for separating undesired matter from blood cells. The second fluid path 38 bypasses the filtration device 40.

Because of this construction, it is possible to direct fluid into and out of the temporary transfer container 34 in a path that either passes through the filtration device 40 (i.e., through the first fluid path 36) or bypasses the filtration device 40 (i.e., through the second fluid path 38).

The transfer container 34 and fluid paths 36 and 38 are all made of low cost medical grade plastic materials, such as polyvinyl chloride plasticized with DEHP.

It should be appreciated that the filtration assembly 14 can be used to remove all types of undesired materials from different types blood cells, depending upon its particular construction. In the illustrated embodiment, the filtration assembly 14 is intended to remove white blood cells (and preferably also platelets) from the red blood cells prior to storage. In this arrangement, the filtration device 40 includes a housing 42 containing a conventional filtration medium 44 suited for the removal of white blood cells and platelets from red blood cells. The filtration medium 44 can include cotton wool, cellulose acetate or another synthetic fiber like polyester.

Figure 3:
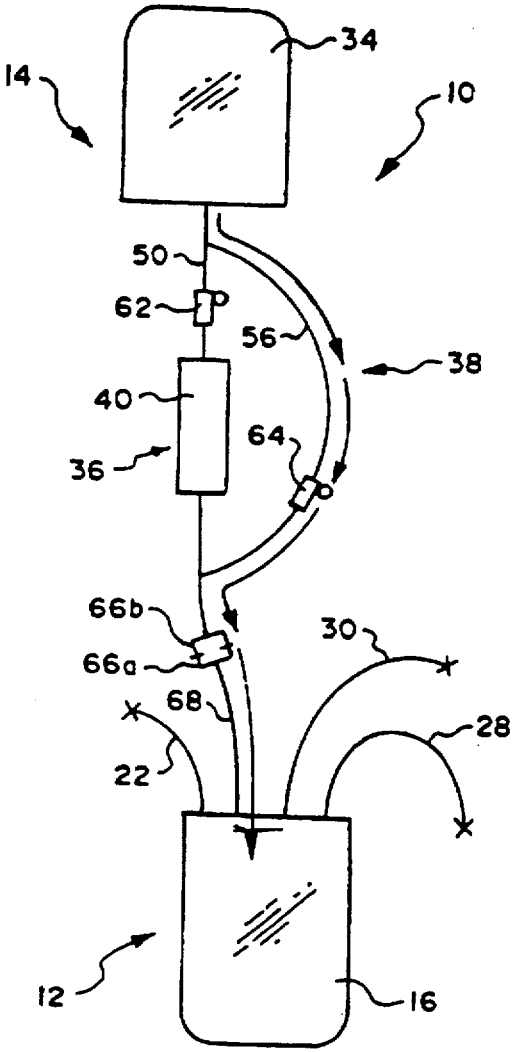
FIG. 3 is a schematic view of the system shown in FIG. 1, with the blood cells, now substantially free of undesired matter, being returned to the blood processing assembly.

The filtration assembly 14 includes flow control means 46 associated with the first and second flow paths 36 and 38. The flow control means 46 is operable in a first mode for directing flow through the first flow path 36, and thus through filtration device 40 (as shown in FIG. 2). The flow control means 46 is also operable in a second mode for directing flow through the second flow path 38, thereby bypassing the filtration device 40 (as shown in FIG. 3).

Figure 4:
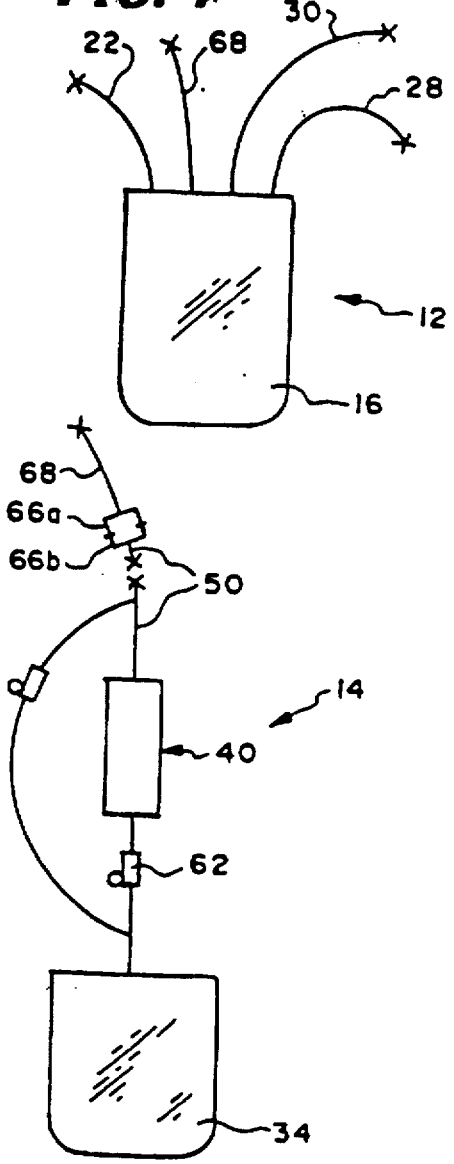
FIG. 4 is a schematic view of the system shown in FIG. 1, with the blood filtration assembly detached from the blood processing assembly after filtration is completed.

In the illustrated and preferred embodiment, a connection assembly 48 is associated with the initially separate blood collection and filtration assemblies 12 and 14. The connection assembly 48 permits selective attachment of the filtration assembly 14 to the blood collection assembly 12. Once attached with the flow control means 46 placed in its first mode (as shown in FIG. 2), red blood cells can be conveyed from the primary container 16 through the first flow path 36 and filtration device 40 into the temporary transfer container 34. In the process, the undesired white cells (and platelets) are removed by the filtration device 40 from the blood cells. Then, while the two assemblies 12 and 14 are still attached together, the flow control means 46 is placed in its second mode, as shown in FIG. 3. The red blood cells, now substantially free of undesired white cells (and platelets), are returned from the temporary transfer container 34 through the second flow path 38, bypassing the filtration device 40, and back into the primary container 16. The filtration assembly 14 is then detached from the blood collection assembly 12, as shown in FIG. 4.

The filtration assembly 14 can be variously constructed. In the illustrated embodiment, the first fluid path 36 takes the form of a length of flexible tubing 50 made of a medical grade plastic material like polyvinyl chloride. The tubing 50 includes first and second opposite end portions 52 and 54. The first end portion 52 is integrally connected to the transfer container 34. The filtration device 40 is located inline between the opposite end portion 54 and the transfer container 34.

In this arrangement, the second fluid path 38 also includes a length of flexible tubing 56 made of a medical grade plastic material like polyvinyl chloride. The tubing 56 also includes opposite end portions 58 and 60. One end portion 60 joins the first fluid path tubing 50 between its second opposite end portion 54 and the filtration device 40. The other end portion 58 joins the first fluid path tubing 50 between the filtration device 40 and the transfer container 34.

In the illustrated embodiment, the flow control means 46 includes a first flow control device 62 in the first flow path 36 between the filtration device 40 and the transfer container 34. The flow control means 46 also includes a second flow control device 64 in the second flow path 38 between the opposite tubing ends 58 and 60. As shown, the second flow control device 64 is preferably located adjacent the tubing end portion 60 that joins the first flow path tubing 50 between its second end portion 54 and the filtration device 40.

In the illustrated embodiment, the flow control devices 62 and 64 are conventional roller clamps that are manually operated to open and close the associated tubing path 50 and 56. In the first mode of operation, the first roller clamp 62 is opened, and the second roller clamp 64 is closed. In the second mode of operation, the opposite is true.

In the illustrated and preferred embodiment, the filtration assembly 14, once sterilized, comprises a sterile, "closed" system (like the processing and storage assembly 12), as judged by the applicable United States standards. In this arrangement, the connection assembly 48 serves to attach and detach the collection and filtration assembly in a manner that preserves the sterile integrity of the closed systems 12 and 14.

More particularly, the connection assembly 48 comprises two mating sterile connection devices (designated 66a and 66b). The devices 66a and 66b (see also FIG. 5) are described in Granzow et al U.S. Pat. Nos. 4,157,723 and 4,265,280, which are incorporated herein by reference. One device 66a is carried by tubing 68 attached to the primary bag 16. The other device 66b is carried at the tubing end 54 of the filtration assembly 14.

Figure 5:
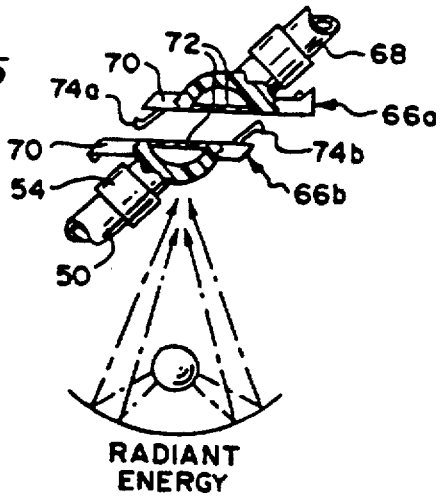
FIG. 5 is an enlarged side sectional view of the sterile connection devices associated with the system shown in FIG. 1.

As shown in FIG. 5, the sterile connection devices 66a and 66b each generally includes a housing 70 having a normally closed, meltable wall 72 made of a radiant energy absorbing material. The housings 70 are joined together with mating bayonet-type couplers 74a and 74b, with the walls 72 placed in facing contact. When connected and exposed to radiant energy, the walls 72 melt at temperatures that result in the destruction of bacteria, while at the same time opening a fluid path between the connected housings 70.

The devices 66a and 66b normally close the associated assemblies 12 and 14 from communication with the atmosphere and are opened in conjunction with an active sterilization step which serves to sterilize the regions adjacent to the interconnecting fluid path as the fluid path is being formed. These devices 66a and 66b also hermetically seal the interconnecting fluid path at the time it is formed. The use of these sterile connection devices 66a and 66b assures a probability of non-sterility that exceeds one in a million. The devices 66a and 66b thus serve to connect the two assemblies 12 and 14 without compromising the sterile integrity of either.

Alternately, the connection assembly 48 can comprise the sterile connecting system disclosed in Spencer U.S. Pat. No. 4,412,835 (not shown). In this arrangement, this system forms a molten seal between the transfer tubing 30 of the primary bag 16 with the tubing end portion 54 of the filtration assembly 14. Once cooled, a sterile weld is formed.

In use, whole blood is collected in the donor bag 16 that forms a part of a blood collection assembly 12. After removal of the platelet-rich plasma and detachment of the transfer bags (see FIG. 2), the donor bag 16 is temporarily attached to the filtration assembly 14 using the associated sterile connection devices 66a and 66b. The first roller clamp 42 is opened, and the second roller clamp 64 is closed.

As shown in FIG. 2, the donor bag 16 is lifted above the temporary transfer bag 34, and the red blood cells are conveyed by gravity flow from the donor bag 16 through the first fluid path 36 and filtration device 40 and into the transfer bag 34. The undesired matter (i.e., white blood cells and platelets) are removed from the red blood cells by the filtration device 40.

It may be necessary to first prime the filter 40 by holding the filter 40 above the donor bag 16 and expressing blood through the filter 40 by squeezing the donor bag 16 until blood flow through the filter 40 is established.

When filtration is completed, the first roller clamp 62 is closed, and the second roller clamp 64 is opened. As shown in FIG. 3, the transfer bag 34 is lifted above the donor bag 12, and the red blood cells, now substantially free of the undesired matter, are returned by gravity flow from the temporary transfer bag 34 through the second fluid path 38, altogether bypassing the filtration device 40, and back into the donor bag 16.

Should air be trapped in the donor bag 16, it may be necessary to first transfer the air through the second path 38 into the transfer bag 34 before returning the red blood cells back to the donor bag 16.

The filtration assembly 14 is then separated from the blood collection assembly 12. This is accomplished by forming snap-apart seals "x" in the tubing 68 of the primary bag 16 and in the tubing 50 of the filtration assembly 14 to remove the connected sterile connection devices 66a and 66b.

In the context of the illustrated embodiment, the entire filtration process (including the attachment and detachment of the filtration assembly 14) can be accomplished in less than five minutes. The red blood cells, now substantially free of the undesired matter, can be stored in the primary bag 16 for transfusion. And, in the preferred embodiment, where the transfer is made using sterile connection techniques, the filtration has occurred without compromising the sterile integrity of the red blood cells or reducing its storage life.

Various features of the invention are set forth in the following claims.

I claim:

1. A method of collecting blood cells, substantially free of undesired matter, comprising the steps of:

collecting a quantity of blood cells in a first container that forms a part of a blood collection system, opening communication between the first container and a separation system that includes a second container, a first fluid path leading into the second container that includes means for separating the undesired matter from the blood cells, and a second fluid path leading into the second container that bypasses the separation means, conveying the blood cells from the first container through the first fluid path and separation means and into the second container, thereby separating the undesired matter from the blood cells, and returning the blood cells, now substantially free of the undesired matter, from the second container through the second fluid path, bypassing the separation means, and back into the first container.

2. A method according to claim 1 wherein the step of opening communication with the separation system includes the step of attaching the filtration system to the blood collection system.

3. A method according to claim 2 wherein the step of attaching the separation system includes the step of employing a sterile connecting assembly that is associated with the separation and blood collection systems.

4. A method according to claim 1 wherein, during the step of conveying blood cells from the first container and into the second container, the first container is located above the second container to convey the blood cells by gravity flow.

5. A method according to claim 4 wherein, during the step of returning blood cells from the second container back to the first container, the second container is located above the first container to return the blood cells by gravity flow.

6. A method according to claim 1 and further including the step, accomplished prior to the step of returning blood cells from the second container back to the first container, of expelling air from the first container into the second container through the second fluid path.

7. A method according to claim 1 and further including the step of storing the blood cells in the first container substantially free of the undesired matter.

8. A method according to claim 1 wherein the blood cells comprise red blood cells and the undesired matter includes white blood cells.

9. A blood collection system comprising a blood collection assembly comprising a primary container for the collection of blood cells, a separation assembly comprising a transfer container, a first fluid path communicating with the transfer container and having an inline separation means for separating undesired matter from blood cells, a second fluid path communicating with the transfer container and bypassing the first fluid path, and flow control means associated with the first and second fluid paths operable in a first mode for directing fluid between the primary and transfer containers through the first fluid path and separation means and in a second mode for directing fluid flow between the primary and transfer containers through the second fluid path bypassing the separation means, and means establishing communication between the separation assembly and the blood collection assembly for conveying, when the flow control means is in its first mode, blood cells from the primary container through the first fluid path and separation means into the transfer container, thereby separating the undesired matter from the blood cells, and to return, when the flow control means is in its second mode, blood cells, now substantially free of the undesired matter, from the transfer container through the second fluid path, bypassing the separation means, and into the primary container.

10. A system according to claim 9 wherein the means for establishing communication includes connection means associated with the separation assembly and the blood collection assembly for attaching and detaching the collection and separation assemblies.

11. A blood collection system according to claim 9 and wherein the blood collection assembly and the separation assembly each comprises a separate closed system, and wherein the means for establishing communication includes connection means associated with the separation assembly and the blood collection assembly for attaching and detaching the collection and separation assemblies in a manner that preserves the sterile integrity of the closed systems.

12. A blood collection system according to claim 9 wherein the first fluid path includes first and second opposite end portions, the first opposite end portion is connected to the transfer container, and the separation means is located in the first fluid path between the second opposite end portion and the transfer container, wherein the second fluid path includes opposite end portions, one of the end portions communicates with the first fluid path between the second opposite end portion and the separation means, and the other one of the end portions communicates with the first fluid path between the separation means and the transfer container.

13. A system according to claim 12 wherein the flow control means includes a first flow control mechanism in the first fluid path between the separation means and the transfer container and a second flow control mechanism in the second fluid path between the opposite ends thereof.

14. A system according to claim 13 wherein the second flow control mechanism is located adjacent the one end portion of the second fluid path that communicates with the first fluid path between the second end portion thereof and the separation means.

15. An assembly usable in association with a primary blood collection and storage container for removing undesired matter from blood cells, the assembly comprising a transfer container, a first fluid path communicating with the transfer container and having an inline separation means for separating undesired matter from blood cells, a second fluid path communicating with the transfer container and bypassing the first fluid path, flow control means associated with the first and second fluid paths operable in a first mode for directing fluid into the transfer container through the first fluid path and separation means and in a second mode for directing fluid from the transfer container through the second fluid path bypassing the separation means, and means establishing communication between the separation assembly and the primary container for conveying, when the flow control means is in its first mode, blood cells from the primary container through the first fluid path and separation means into the transfer container, thereby separating the undesired matter from the blood cells, and to return, when the flow control means is in its second mode, blood cells, now substantially free of the undesired matter, from the transfer container through the second fluid path, bypassing the separation means, and into the primary container.

16. An assembly according to claim 15 wherein the transfer container is free of fluid prior to use.

17. An assembly according to claim 15 wherein the first fluid path includes first and second opposite end portions, the first opposite end portion is connected to the transfer container, and the separation means is located in the first fluid path between the second opposite end portion and the transfer container, wherein the second fluid path includes opposite end portions, one of the end portions communicates with the first fluid path between the second opposite end portion and the separation means, and the other one of the end portions communicates with the first fluid path between the separation means and the transfer container.

18. A system according to claim 17 wherein the flow control means includes a first flow control mechanism in the first fluid path between the separation means and the transfer container and a second flow control mechanism in the second fluid path between the opposite ends thereof.

19. A system according to claim 18 wherein the second flow control mechanism is located adjacent the one end portion of the second fluid path that communicates with the first fluid path between the second end portion thereof and the separation means.

20. A blood collection system according to claim 15 and wherein the assembly comprises a sterile, closed system, and wherein the means for establishing communication includes connection means for attaching and detaching the assembly to the primary container in a manner that preserves the sterile integrity of the system.

*21. An assembly for removing undesired matter from blood cells comprising*

*a filter body having an inlet and an outlet,*

*filtration medium in the filter body for removing undesired matter from blood cells,*

*an inlet fluid path communicating with the inlet of the filter body and including means for attaching a first container holding a quantity of blood cells for conveying blood cells from the first container to the filtration medium for the removal of undesired matter,*

*an outlet fluid path communicating with the outlet of the filter body for conveying blood cells from the filtration medium substantially free of undesired matter, the outlet fluid path including a second container for receiving blood cells substantially free of undesired matter, and*

*a bypass path having opposite ends, one end being attached to the inlet fluid path between the first container and the inlet of the filter body and the opposite end being attached to the outlet fluid path between the second container and the outlet of the filter body for venting air without transferring liquid between the inlet fluid path and the outlet fluid path, bypassing the filtration medium in the filter body.*

*22. An assembly according to claim 21*

*and further including flow control means in the bypass path operable to open and close the bypass path.*

*23. An assembly for removing undesired matter from blood cells comprising*

*a filter body having an interior and inlet and an outlet,*

*filtration medium in the body interior for removing undesired matter from blood cells,*

*inlet tubing communicating with the inlet of the filter body and including means for attaching a first container holding a quantity of blood cells for conveying blood cells from the first container to the filtration medium for the removal of undesired matter,*

*outlet tubing communicating with the outlet of the filter body for conveying blood cells from the filtration medium substantially free of undesired matter, the outlet tubing including a second container for receiving blood cells substantially free of undesired matter, and*

*a length of tubing extending outside the filter body with one end attached to the inlet tubing between the filter inlet and the first container and the opposite end attached to the outlet tubing between the filter outlet and the second container for conveying air without transferring liquid between the inlet tubing and the outlet tubing in a path that bypasses the interior of the filter body.*

*24. An assembly according to claim 23*

*and further including flow control means in the length of tubing operable to open and close the length of tubing.*

* * * * *